(12) United States Patent
Foley

(10) Patent No.: US 10,722,227 B2
(45) Date of Patent: Jul. 28, 2020

(54) MEDICAL DEVICE FOR USE IN THE CREATION OF A TEMPORARY PNEUMOPERITONEUM

(71) Applicant: Dome Medical Technologies, Inc., New York, NY (US)

(72) Inventor: Glenn S. Foley, Vancouver, WA (US)

(73) Assignee: Dome Medical Technologies, Inc., New York, NY (US)

( * ) Notice: Subject to any disclaimer, the term of this patent is extended or adjusted under 35 U.S.C. 154(b) by 0 days.

(21) Appl. No.: 16/031,854

(22) Filed: Jul. 10, 2018

(65) Prior Publication Data

US 2018/0317903 A1    Nov. 8, 2018

Related U.S. Application Data

(63) Continuation of application No. 15/310,347, filed as application No. PCT/EP2015/000997 on May 15, 2015, now abandoned.

(30) Foreign Application Priority Data

May 16, 2014   (GB) .................................. 1408740.7

(51) Int. Cl.
| | |
|---|---|
| *A61B 17/02* | (2006.01) |
| *A61B 17/34* | (2006.01) |
| *A61B 90/40* | (2016.01) |
| *A61B 17/30* | (2006.01) |

(52) U.S. Cl.
CPC .......... *A61B 17/0281* (2013.01); *A61B 17/30* (2013.01); *A61B 17/3462* (2013.01); *A61B 17/3474* (2013.01); *A61B 90/40* (2016.02); *A61B 17/3423* (2013.01); *A61B 2017/308* (2013.01)

(58) Field of Classification Search
CPC ........................ A61B 17/0281; A61B 17/3423
See application file for complete search history.

(56) References Cited

U.S. PATENT DOCUMENTS

| | | | | |
|---|---|---|---|---|
| 5,813,409 | A * | 9/1998 | Leahy ................ | A61B 17/3423 128/850 |
| 2007/0270745 | A1* | 11/2007 | Nezhat ................ | A61B 5/6834 604/115 |
| 2010/0113886 | A1* | 5/2010 | Piskun ............... | A61B 17/3421 600/231 |

* cited by examiner

*Primary Examiner* — Nicholas J Plionis
(74) *Attorney, Agent, or Firm* — Miller IP Law, LLC

(57) ABSTRACT

A medical device for use in the creation of a temporary pneumoperitoneum includes a substantially dome-shaped body having a vacuum port providing a fluid passageway between an underside of the dome-shaped body and an upside of the dome-shaped body. A frustoconical port is provide in the domed-shaped body for reception and through passage of one or more pieces of associated medical apparatus therethrough.

14 Claims, 2 Drawing Sheets

MEDICAL DEVICE FOR USE IN THE CREATION OF A TEMPORARY PNEUMOPERITONEUM

This invention relates to a medical device for use in the creation of a temporary pneumoperitoneum.

A laparoscopic surgical procedure is often preferred to a laparotomy due to shorter recovery times and the reduced adverse impact that it has on the patient's wellbeing. As part of the laparoscopic surgical procedure, a temporary pneumoperitoneum is formed in the patient's abdomen to separate the skin, tissue and muscle from the organs in the abdominal cavity below. This is achieved by insufflating the patient's abdomen with an inert gas, usually carbon dioxide ($CO_2$).

Before insufflating the patient's abdomen with the inert gas, the skin, subcutaneous tissue and muscle are separated from the organs in the abdominal cavity below by applying a vacuum to the patient's abdomen. Once separated, a gas delivery needle can be inserted into the resulting space between the organs and the skin, tissue and muscle and the inert gas can be pumped into that space to stabilize and maintain the temporary pneumoperitoneum.

Heretofore, a number of devices have been proposed for the application of a vacuum to the patient's abdomen. One such device is that described in US2008/0058851 in the name of Edelstein et al. Another such device is that described in U.S. Pat. No. 7,585,281 in the name of Nezhat et al. A third such device is that described in WO2011/128713 filed in the name of Medical Device International Limited and having the same inventor as the present application. Although these devices all possess advantageous aspects over alternative ways of separating the skin, subcutaneous tissue and muscle from the organs, there are also disadvantages to the known devices. Most importantly, the known devices restrict the movement of a medical apparatus inserted through the device into the patient's abdomen and allow little or no room for positional adjustment of the medical apparatus. Secondly, some of the known devices have a relatively complex construction which increases the cost of manufacture. As these devices are intended to be disposable, a low manufacturing cost is essential.

It is an aim of the present invention to provide a medical device for use in the creation of a temporary pneumoperitoneum that overcomes at least some of the problems with the known devices. It is a further aim of the present invention to provide a medical device for use in the creation of a temporary pneumoperitoneum that offers a useful alternative to the consumer.

According to the invention there is provided a medical device for use in the creation of a temporary pneumoperitoneum, the medical device comprising a substantially dome-shaped body having a vacuum port providing a fluid passageway between the underside of the dome-shaped body and the upside of the dome-shaped body, the dome-shaped body further comprising a frustoconical port for reception and throughpassage of one or more pieces of medical apparatus therethrough.

The underside of the dome-shaped body is intended to mean the side closest to the patient's body, whilst the upside is intended to mean the side furthest from the patient's body.

As bodies vary from patient to patient, it is difficult to predict precisely how a medical device will settle on the patient's body, for example their abdomen, once the vacuum is applied. With the known devices, a degree of trial and error is sometimes required to ensure that the medical apparatus for insertion through the medical device will be correctly aligned with the part of the abdomen being targeted. In other cases, the medical apparatus will be positioned sub-optimally. By having a device according to the present invention with a frustoconical port, it will be possible for the surgical team to adjust the position and the orientation of the medical apparatus inserted through the frustoconical port of the medical device with relative ease. The direction of the medical apparatus can be adjusted from side to side through an arc of close to 180° and the distal tip of the medical apparatus can be rotated around in a circle through 360°, allowing for very precise placement of the medical apparatus. Furthermore, such adjustability will allow for more forgiving placement of the medical device on the patients abdomen. These will speed up the surgical procedure and greatly facilitate the performance of the surgical procedure.

The dome-shaped body will generally be constructed from a material that is suitably robust and rigid that can withstand significant vacuum pressures without collapsing inwardly onto the patient's abdomen. It is envisaged that the dome-shaped body can be constructed from a plastics material for this purpose, for example, a medical grade polycarbonate or equivalent material. The body is described throughout as being dome-shaped and indeed this is preferable for the spread of the vacuum induced forces in the body. However, other shapes of body are envisaged and may be put to good use instead of a strictly dome-shaped body.

In one embodiment of the invention there is provided a medical device in which the frustoconical port is closed. This is seen as a particularly useful aspect of the present invention. By having a closed port, the vacuum can be created faster and with greater ease. Secondly, the device will tend to settle more predictably on the patient's abdomen due to the fact that air is not being drawn into the device from another location on the dome-shaped body. Furthermore, there will be less chance of ingress of foreign bodies into the abdominal cavity.

In one embodiment of the invention there is provided a medical device in which the frustoconical port is closed with a plug. A plug may be inserted with ease into the frustoconical port to close the port during manufacture. The plug may be formed from a different material to the remainder of the dome-shaped body which can be advantageous for a number of reasons. For example, the plug can be constructed from a material that will be easier to puncture than the remainder of the dome-shaped body, thereby facilitating insertion of the medical apparatus through the port. Furthermore, the plug may be constructed from a material impregnated with an antibacterial agent to obviate the possibility of the medical apparatus being inserted into the patient causing an infection. Similarly, the plug may be impregnated with a local anaesthetic to numb the area of the patient's abdomen that comes into contact with the plug.

In one embodiment of the invention there is provided a medical device in which the plug comprises a penetrable barrier. By "penetrable", what is meant is a barrier that it will be possible to penetrate with relative ease using a medical instrument such as a needle or the like. In a preferred embodiment, the penetrable material comprises a softer material than the dome-shaped body, for example a semi-latex material. A semi-latex material is understood to be one which contains chains of latex polymer but do not cause hypoallergenic issues. The penetrable material may alternatively comprise a non-latex polymer material. In certain instances, the materials used for the dome-shaped body and the plug will be biodegradable and suitable for disposal after the device has been used. The manufacturing method will be highly cost effective due in large part to the simplicity of the manufacturing process (a two stage mould process) and this will contribute to a very cost effective medical device.

In one embodiment of the invention there is provided a medical device in which the frustoconical port is a blind bore formed in the dome-shaped body. This is seen as a useful alternative as apart from the vacuum port, the dome-shaped body will not have any apertures through which air can pass. This will facilitate the creation of the vacuum and when necessary, the medical apparatus can be used to puncture through the dome-shaped body at the base of the blind bore.

In one embodiment of the invention there is provided a medical device in which there is provided a target located on the upside of the dome-shaped body coincident with and concentric with the frustoconical port. By providing a target, the user will be able to locate the frustoconical port with relative ease, thereby facilitating the operation of the device.

In one embodiment of the invention there is provided a medical device in which the thickness of the dome-shaped body at the base of the blind bore is less than or equal to 5 mm thick. By having the dome-shaped body no more than 5 mm thick at this point, the dome shaped body can be punctured with relative ease. Ideally, the thickness of the dome-shaped body at the base of the blind bore is less than or equal to 1.5 mm thick.

In one embodiment of the invention there is provided a medical device in which the frustoconical port opens outwardly in the direction from the upside of the dome-shaped body to the underside of the dome-shaped body. This is seen as a preferred orientation of the frustoconical port as the opening at the upside of the dome-shaped body can still be relatively small which is good for particle ingress prevention and will allow for a more steady engagement of the medical apparatus passed through the frustoconical port in due course.

In one embodiment of the invention there is provided a medical device in which there is provided a second frustoconical port on the dome-shaped body located above and coincident with the first frustoconical port, the second frustoconical port opens outwardly in the direction from the underside of the dome-shaped body to the upside of the dome-shaped body, the pair of frustoconical ports thereby combining to form a substantially hourglass-shaped port for reception and throughpassage of one or more pieces of medical apparatus therethrough.

In one embodiment of the invention there is provided a medical device in which the dome-shaped body further comprises another frustoconical port for reception and throughpassage of one or more pieces of medical apparatus therethrough. Another frustoconical port will allow for other pieces of equipment to be inserted into the abdominal cavity from other directions, thereby facilitating certain surgical procedures.

In one embodiment of the invention there is provided a medical device in which the frustoconical port is located substantially centrally at the axis of the dome-shaped body. If another frustoconical port is provided it may be located on the side of the dome-shaped body spaced apart from the first frustoconical port.

In one embodiment of the invention there is provided a medical device in which there is provided an annular flange at the base of the dome-shaped body. The annular flange may be outwardly depending from the base of the dome-shaped body. The flange will allow for a secure seal to be formed between the base of the dome-shaped body and the patient's abdomen facilitating vacuum creation and retention and also reducing bruising to the patient's abdomen. Alternatively, the thickness of the dome-shaped body at the base could be dimensioned so that it performs the same function as the annular flange. Further still, the annular flange could be inwardly depending rather than outwardly depending.

In one embodiment of the invention there is provided a medical device in which the dome-shaped body is saucer dome-shaped. A saucer dome-shape may be more suited ergonomically to certain body types and may be easier for the patient's body to mould into.

Whilst reference has been made to a medical device for use in the creation of a temporary pneumoperitoneum in abdominal procedures, it will be understood that the medical device described herein may also be used in other areas where key-hole surgery is performed. The dome shaped housing may be resized accordingly so that it will form a suitable seal with the patient's body around the area to be operated upon.

The invention will now be more clearly understood from the following description of some embodiments thereof given by way of example only and with reference to the accompanying drawings, in which:—

Figure 1:
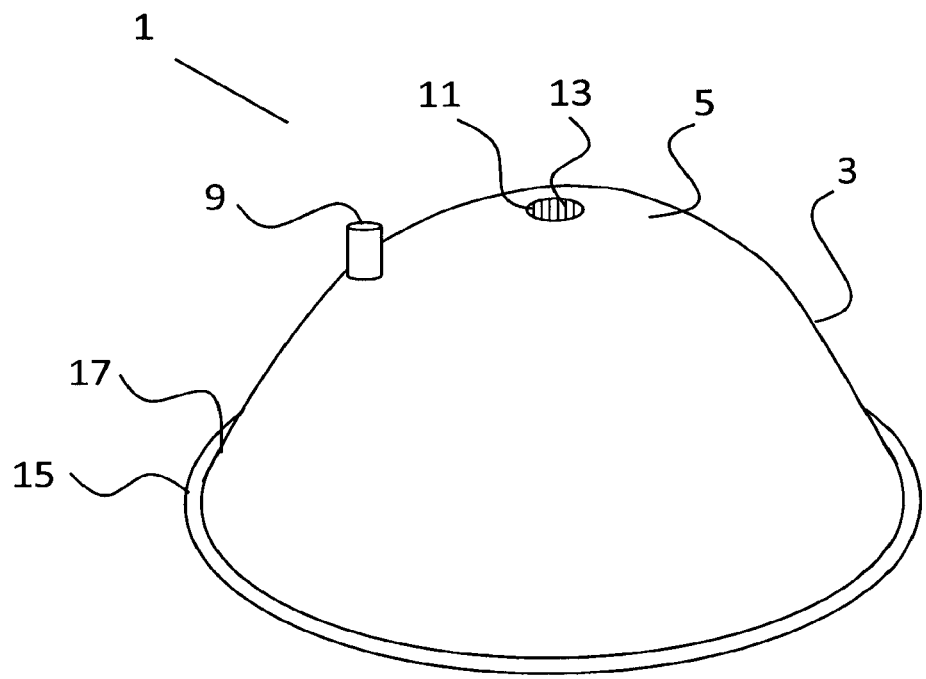
FIG. 1 is a perspective view of a medical device for use in the creation of a temporary pneumoperitoneum according to an embodiment of the invention.
Figure 2:
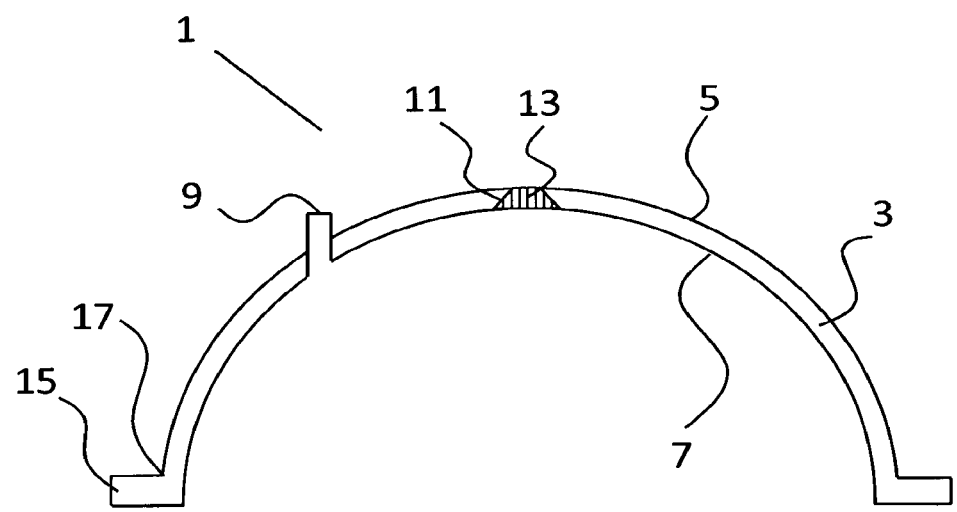
FIG. 2 is a side cross-sectional view of the medical device of FIG. 1.

Referring to FIGS. 1 and 2, there is shown a medical device for use in the creation of a temporary pneumoperitoneum, indicated generally by the reference numeral 1, the medical device comprising a substantially dome-shaped body 3 having an upside 5, an underside 7, and a vacuum port 9 providing a fluid passageway between the upside 5 and the underside 7. The dome-shaped body 3 further comprises a port 11 for reception and throughpassage of one or more pieces of medical apparatus (not shown) therethrough. The port 11 is frustoconically shaped with the port widening in the direction from the upside 5 to the underside 7. By having a frustoconical port 11, a medical apparatus (not shown) inserted therethrough may be directionally adjusted in order to allow the medical apparatus to be positioned more accurately without requiring adjustment of the entire medical device 1.

A plug 13 is mounted in the frustoconical port 11, thereby closing the port. The plug 13 is constructed from a penetrable barrier material that will allow a medical apparatus to be pushed therethrough. The dome-shaped body 3 has an annular flange 15 at the base 17 thereof. The annular flange 15 is outwardly depending from the base 17 of the dome-shaped body 3. Potentially, a suitable hypoallergenic covering may be provided on the underside of the dome-shaped body and more importantly on the underside of the annular flange.

In use, the medical device for use in the creation of a temporary pneumoperitoneum 1 is placed on the abdomen of a patient (not shown). The annular flange 15 forms a seal with the patient's abdomen. A vacuum/suction device is connected up to the vacuum port 9 and air is removed from between the underside 7 of the dome-shaped body 3 and the patient's abdomen. As the air is removed, the patient's abdomen will be drawn upwards towards the underside of the dome-shaped body. This has the effect of separating the skin, subcutaneous tissue and muscle from the organs in the abdominal cavity below. A needle (not shown) or similar device is then inserted through the plug 13 in the frustoconical port 11 and into the patient's abdomen. A camera may be mounted on the needle to allow the surgeon to monitor the location of the distal tip of the needle. Once the distal tip of the needle is in the desired location within the patient's abdomen, an inert gas, typically $CO_2$, is delivered into the cavity in the patient's abdomen, thereby forming the temporary pneumoperitoneum. The desired surgical procedure is then performed.

The dome-shaped body 3 may be left in situ throughout the surgical procedure or alternatively it may be removed if desired. If the dome-shaped body is left in situ, the frustoconical port should be large enough to allow more than one medical apparatus therethrough to allow the operation to be performed. Once the operation is finished, the dome shaped body 3 may be discarded.

Figure 3:
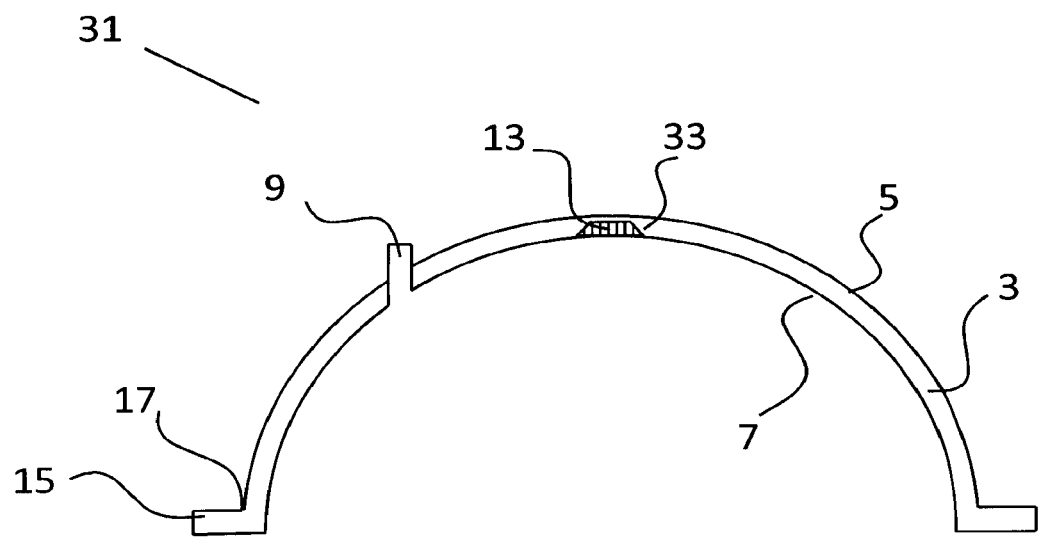
FIG. 3 is a side cross-sectional view of a second embodiment of a medical device according to the invention.

Referring to FIG. 3, there is shown an alternative embodiment of a medical device (second embodiment), indicated generally by the reference numeral 31, in which like parts have been given the same reference numeral as before. In the embodiment shown, the frustoconical bore 33 is a blind bore. In other words, the frustoconical bore 33 does not extend through the dome-shaped body. In this implementation, a target (not shown) will preferably be provided, either printed or scored into the upside of the dome-shaped body coincident and concentric with the frustoconical port 33. Again, a plug 13 is provided in the frustoconical bore 33. The thickness of the dome-shaped body at the base of the blind bore 33 will be of an appropriate thickness that will allow piercing by one or more of a plurality of medical devices. Preferably, the thickness of the dome-shaped body at the base of the blind bore will be of the order of 1.5 mm ($1.5 \times 10^{-3}$ m). By having the bore closed in this fashion, the vacuum can be created in a more effective manner.

Figure 4:
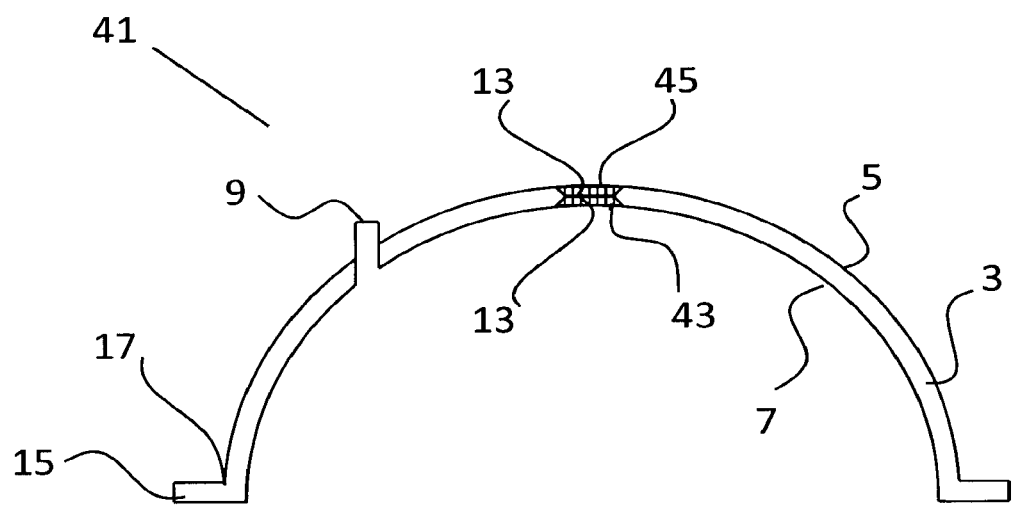
FIG. 4 is a side cross-sectional view of a third embodiment of a medical device according to the invention.

Referring to FIG. 4, there is shown a further alternative embodiment of a medical device (third embodiment), indicated generally by the reference numeral 41, in which like parts have been given the same reference numeral as before. In the embodiment shown, there is provided a second frustoconical port 45 located above and coincident with the first frustoconical port 43. The two frustoconical ports are arranged face to face so that together the two frustoconical ports 43, 45 form an hourglass shaped port. If desired, the frustoconical ports 43, 45 may be blind bores separated by a dividing wall therebetween.

Various modifications could be made to the above described embodiments without departing from the scope of the present invention as defined in the claims. For example, another port could be provided elsewhere on the device 1, 31, 41 to allow a second medical apparatus to be inserted into the patient's cavity from an alternative angle than the first medical apparatus. In the embodiments shown, there is provided an annular flange 15 however if desired the thickness of the dome-shaped body at the base could be dimensioned so that it performs the same function as the annular flange. Further still, the annular flange could be inwardly depending rather than outwardly depending.

The dome-shaped body will generally be constructed from a material that is suitably robust and rigid that can withstand significant vacuum pressures without collapsing inwardly onto the patient's abdomen. It is envisaged that the dome-shaped body can be constructed from a plastics material for this purpose, for example, a medical grade polycarbonate or equivalent material. The body is described throughout as being dome-shaped and indeed this is preferable for the spread of the vacuum induced forces on the body. However, other shapes of body are envisaged and may be put to good use instead of a strictly dome-shaped body.

The penetrable plug 13 will preferably be provided by a softer material than the dome-shaped body, for example, the penetrable plug could be constructed from latex, or more preferably from semi-latex or a non-latex polymer material. In certain instances, the materials used for the dome-shaped body and the plug will be biodegradable and suitable for disposal after the device has been used. The manufacturing method will be highly cost effective due in large part to the simplicity of the manufacturing process (a two stage mould process) and this will contribute to a very cost effective medical device.

Throughout this specification, reference has been made to a medical device for use in the creation of a temporary pneumoperitoneum in abdominal procedures however it will be understood that the medical device described herein may also be used in other areas where key-hole surgery is performed. The dome shaped housing may be resized where key-hole surgery is performed. The dome shaped housing may be resized accordingly so that it will form a suitable seal with the patient's body around the area to be operated upon.

In this specification the terms "comprise, comprises, comprised and comprising" and the terms "include, includes, included and including" are all deemed totally interchangeable and should be afforded the widest possible interpretation.

The invention is in no way limited to the embodiments hereinbefore described but may be varied in both construction and detail within the scope of the claims.

The invention claimed is:
1. A device, comprising:
a rigid dome-shaped body;
a vacuum port through the rigid dome-shaped body providing a fluid passageway between an underside of the dome-shaped body and an upside of the dome-shaped body;
an hourglass-shaped blind bore in the rigid dome-shaped body for reception and throughpassage of one or more pieces of associated medical apparatus therethrough, wherein:
the hourglass-shaped blind bore is separate from the vacuum port and extends into the dome-shaped body from the underside of the dome-shaped body and the upside of the dome-shaped body; and
the rigid dome-shaped body forms a dividing wall between an upside of the hourglass-shaped blind bore and an underside of the hourglass-shaped blind bore; and
a plug disposed in the upside of the hourglass-shaped blind bore or the underside of the hourglass-shaped blind bore, wherein the plug comprises a penetrable barrier.

2. The device of claim 1, wherein the underside of the hourglass-shaped blind bore comprises a first frustoconical opening that opens away from the rigid dome-shaped body towards the underside of the dome-shaped body.

3. The device of claim 2, wherein:
the upside of the hourglass-shaped blind bore comprises a second frustoconical opening on the rigid dome-shaped body located above and coincident with the first frustoconical opening; and
the second frustoconical opening opens away from the rigid dome-shaped body towards the upside of the dome-shaped body, the first and second frustoconical openings thereby combining to form the hourglass-shaped blind bore for reception and throughpassage of the one or more pieces of associated medical apparatus therethrough.

4. The device of claim 1, wherein the dome-shaped body further comprises an additional port for reception and throughpassage of the one or more pieces of associated medical apparatus therethrough.

5. The device of claim 4, wherein:
the hourglass-shaped blind bore is located at an apex of the rigid dome-shaped body; and
the additional port is located on a side of the dome-shaped body spaced apart from the hourglass-shaped blind bore.

6. The device of claim 1, wherein there is provided an annular flange located at a base of the rigid dome-shaped body.

7. An apparatus, comprising:
a rigid dome-shaped body;
a vacuum port through the rigid dome-shaped body providing a fluid passageway between an underside of the dome-shaped body and an upside of the dome-shaped body;
an hourglass-shaped blind bore in the rigid dome-shaped body for reception and throughpassage of an associated medical apparatus therethrough, wherein:
the hourglass-shaped blind bore is separate from the vacuum port and extends into the dome-shaped body from the underside of the dome-shaped body and the upside of the dome-shaped body, wherein:
the underside of the hourglass-shaped blind bore comprises a first frustoconical opening that opens away from the rigid dome-shaped body towards the underside of the dome-shaped body; and
the upside of the hourglass-shaped blind bore comprises a second frustoconical opening on the rigid dome-shaped body located above and coincident with the first frustoconical opening, wherein the second frustoconical opening opens away from the rigid dome-shaped body towards the upside of the dome-shaped body, the first and second frustoconical openings thereby combining to form the hourglass-shaped blind bore for reception and throughpassage of the associated medical apparatus therethrough;
the rigid dome-shaped body forms a dividing wall between an upside of the hourglass-shaped blind bore and an underside of the hourglass-shaped blind bore; and
a plug disposed in the upside of the hourglass-shaped blind bore or the underside of the hourglass-shaped blind bore, wherein the plug comprises a penetrable barrier.

8. The apparatus of claim 7, wherein the dome-shaped body further comprises an additional port for reception and throughpassage of the associated medical apparatus therethrough.

9. The apparatus of claim 8, wherein:
the hourglass-shaped blind bore is located at an apex of the rigid dome-shaped body; and
the additional port is located on a side of the dome-shaped body spaced apart from the hourglass-shaped blind bore.

10. The apparatus of claim 7, further comprising an annular flange located at a base of the rigid dome-shaped body.

11. The apparatus of claim 7, wherein:
the dome-shaped body further comprises an additional port for reception and throughpassage of the one or more pieces of associated medical apparatus therethrough; and
the hourglass-shaped blind bore is located at an apex of the rigid dome-shaped body and the additional port is located on a side of the dome-shaped body spaced apart from the hourglass-shaped blind bore.

12. An apparatus, comprising:
a rigid dome-shaped body;
a vacuum port through the rigid dome-shaped body providing a fluid passageway between an underside of the dome-shaped body and an upside of the dome-shaped body;
an hourglass-shaped blind bore in the rigid dome-shaped body for reception and throughpassage of one or more pieces of associated medical apparatus therethrough, wherein:
the hourglass-shaped blind bore is separate from the vacuum port and extends into the dome-shaped body from the underside of the dome-shaped body and the upside of the dome-shaped body;
the rigid dome-shaped body forms a dividing wall between an upside of the hourglass-shaped blind bore and an underside of the hourglass-shaped blind bore; and
a plug disposed in the upside of the hourglass-shaped blind bore or the underside of the hourglass-shaped blind bore, the plug comprising a penetrable barrier, wherein:
the plug is a softer material than the rigid dome-shaped body;
the materials used for the dome-shaped body is biodegradable; and
the plug is biodegradable.

13. The apparatus of claim 12, wherein the plug is latex material, semi-latex material, or a non-latex polymer material.

14. The apparatus of claim 12, wherein:
the underside of the hourglass-shaped blind bore comprises a first frustoconical opening that opens away from the rigid dome-shaped body towards the underside of the dome-shaped body; and
the upside of the hourglass-shaped blind bore comprises a second frustoconical opening on the rigid dome-shaped body located above and coincident with the first frustoconical opening, wherein the second frustoconical opening opens away from the rigid dome-shaped body towards the upside of the dome-shaped body, the first and second frustoconical openings thereby combining to form the hourglass-shaped blind bore for reception and throughpassage of an associated medical apparatus therethrough.

* * * * *